US010947278B2

(12) United States Patent
Lee

(10) Patent No.: US 10,947,278 B2
(45) **Date of Patent: *Mar. 16, 2021**

(54) RECOMBINANT VECTOR COMPRISING PORCINE FC FRAGMENT AND PREPARATION METHOD OF RECOMBINANT PROTEIN USING THEREOF

(71) Applicant: BIOAPPLICATIONS INC., Pohang-si (KR)

(72) Inventor: Yongjik Lee, Pohang-si (KR)

(73) Assignee: BIOAPPLICATIONS INC., Pohang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,991

(22) Filed: Apr. 3, 2019

(65) Prior Publication Data

US 2020/0087351 A1 Mar. 19, 2020

Related U.S. Application Data

(63) Continuation of application No. PCT/KR2018/015398, filed on Dec. 6, 2018.

(30) Foreign Application Priority Data

Sep. 19, 2018 (KR) ........................ 10-2018-0112442

(51) Int. Cl.

| | |
|---|---|
| ***C12P 21/02*** | (2006.01) |
| ***A01K 67/00*** | (2006.01) |
| ***A01K 67/033*** | (2006.01) |
| ***C07K 14/005*** | (2006.01) |
| ***C07K 14/705*** | (2006.01) |

(52) U.S. Cl.

CPC .......... *C07K 14/005* (2013.01); *C07K 14/705* (2013.01); *C07K 2319/30* (2013.01); *C12N 2710/22022* (2013.01); *C12N 2750/10022* (2013.01); *C12N 2770/24222* (2013.01)

(58) Field of Classification Search

CPC .......................... C07K 14/705; C07K 2319/30
USPC ........................................................ 424/69.7
See application file for complete search history.

(56) References Cited

U.S. PATENT DOCUMENTS

| | | | | |
|---|---|---|---|---|
| 8,784,834 B2 * | 7/2014 | Kuo | C07K 14/555 | 424/185.1 |
| 2016/0193295 A1 * | 7/2016 | Kannan | A61K 38/18 | 530/387.3 |

FOREIGN PATENT DOCUMENTS

| | | |
|---|---|---|
| KR | 10-2009-0030964 A | 3/2009 |
| KR | 10-2014-0073710 A | 6/2014 |
| KR | 10-2016-0077239 A | 7/2016 |
| KR | 10-2016-0123145 A | 10/2016 |

OTHER PUBLICATIONS

Flanagan (Methods in Molecular Biology, 2007, 378:33-52).*
De Wilde (Plant Physiology, 2013, 161:1021-1033).*
NCBI, GenBank Accession No. BAM66310.1, 'IgG heavy chain constant region,partial [Sus scrofa]', Jan. 25, 2018.

* cited by examiner

*Primary Examiner* — Valarie E Bertoglio
(74) *Attorney, Agent, or Firm* — Vorys, Sater, Seymour & Pease LLP; Mih Suhn Koh

(57) ABSTRACT

Provided is a recombinant vector including a porcine Fc fragment. By fusing the porcine Fc fragment with various target proteins by using the recombinant vector of the present invention, not only target proteins may be expressed using various hosts including plants, but the productivity and stability of target proteins may also be increased.

7 Claims, 8 Drawing Sheets

Specification includes a Sequence Listing.

SEQUENCE LISTING

```
<160> NUMBER OF SEQ ID NOS: 19

<210> SEQ ID NO 1
<211> LENGTH: 690
<212> TYPE: DNA
<213> ORGANISM: Artificial Sequence
<220> FEATURE:
<223> OTHER INFORMATION: DNA sequence of pFc1

<400> SEQUENCE: 1

ggaactaaga ctaagccacc ttgtcctatt tgtccagggt gcgaggtagc cggtcccagc      60

gtgtttattt ttccaccaaa accaaaggat actttgatga tatctcaaac accggaagtt     120

acttgcgttg tggtcgacgt ttcaaaagag catgccgaag ttcagttctc ttggtatgtg     180

gatggtgtgg aagtgcacac cgctgagaca cgtcctaaag aggaacagtt taactctact     240

tacagagtcg tgtccgtatt gcccattcag catcaagact ggcttaaggg aaaagaattt     300

aaatgtaagg taaataatgt tgatctgcca gcacctataa ctagaaccat ctcgaaagct     360

attggacaat ctagagaacc tcaagtttat acattgcctc ctccagctga ggaactttct     420

agaagtaaag tcactgttac atgcttagtt attggattct atccaccaga tatccatgtt     480

gaatggaaat caaatggtca gcccgaacct gagggcaact acagaacaac accaccacag     540

caagatgtag atggtacttt tttcctctac tcaaaactag ctgttgataa ggctaggtgg     600

gatcatggcg agacatttga gtgtgcagtc atgcacgaag cacttcataa tcactatacc     660

caaaagtcca taagtaagac gcaaggaaag                                      690


<210> SEQ ID NO 2
<211> LENGTH: 230
```

-continued

<212> TYPE: PRT
<213> ORGANISM: Artificial Sequence
<220> FEATURE:
<223> OTHER INFORMATION: Amino acid sequence of pFc1

<400> SEQUENCE: 2

```
Gly Thr Lys Thr Lys Pro Pro Cys Pro Ile Cys Pro Gly Cys Glu Val
1               5                   10                  15

Ala Gly Pro Ser Val Phe Ile Phe Pro Pro Lys Pro Lys Asp Thr Leu
            20                  25                  30

Met Ile Ser Gln Thr Pro Glu Val Thr Cys Val Val Val Asp Val Ser
        35                  40                  45

Lys Glu His Ala Glu Val Gln Phe Ser Trp Tyr Val Asp Gly Val Glu
    50                  55                  60

Val His Thr Ala Glu Thr Arg Pro Lys Glu Glu Gln Phe Asn Ser Thr
65                  70                  75                  80

Tyr Arg Val Val Ser Val Leu Pro Ile Gln His Gln Asp Trp Leu Lys
                85                  90                  95

Gly Lys Glu Phe Lys Cys Lys Val Asn Asn Val Asp Leu Pro Ala Pro
            100                 105                 110

Ile Thr Arg Thr Ile Ser Lys Ala Ile Gly Gln Ser Arg Glu Pro Gln
        115                 120                 125

Val Tyr Thr Leu Pro Pro Pro Ala Glu Glu Leu Ser Arg Ser Lys Val
    130                 135                 140

Thr Val Thr Cys Leu Val Ile Gly Phe Tyr Pro Pro Asp Ile His Val
145                 150                 155                 160

Glu Trp Lys Ser Asn Gly Gln Pro Glu Pro Glu Gly Asn Tyr Arg Thr
                165                 170                 175

Thr Pro Pro Gln Gln Asp Val Asp Gly Thr Phe Phe Leu Tyr Ser Lys
            180                 185                 190

Leu Ala Val Asp Lys Ala Arg Trp Asp His Gly Glu Thr Phe Glu Cys
        195                 200                 205

Ala Val Met His Glu Ala Leu His Asn His Tyr Thr Gln Lys Ser Ile
    210                 215                 220

Ser Lys Thr Gln Gly Lys
225                 230
```

<210> SEQ ID NO 3
<211> LENGTH: 681
<212> TYPE: DNA
<213> ORGANISM: Artificial Sequence
<220> FEATURE:
<223> OTHER INFORMATION: DNA sequence of pFc2

<400> SEQUENCE: 3

```
gttggaagac catgccctat atgtcctgct tgtgaaggtc caggtccctc tgcttttata     60

ttcccaccaa agccgaagga taccttgatg atttcacgta caccacaagt tacttgtgtt    120

gttgtggatg tttcacaaga aaatcctgag gtacaattca gctggtatgt tgatggggta    180

gaagtgcaca ctgcacagac tcgaccaaag gaggcccagt ttaactcgac ttatagagtt    240

gtttctgttc tcccaatcca acacgaagat tggctgaagg gcaaggaatt tgaatgcaag    300

gttaacaata aagatctacc agcaccaatt accaggatta tttctaaggc aaaaggaccc    360

tccagagagc cccaagttta cacattgtct ccttctgctg aggagcttag tagaagtaaa    420

gtgagcatta cctgcttagt gacgggattc taccctccag acatcgacgt cgaatggaaa    480

tctaatggtc aacctgagcc agaaggtaac tataggacta ctccaccaca acaggacgtc    540
```

```
gatggcacat actttcttta ttcaaaactt gctgtcgata aggcaagttg gcaaagagga    600

gatccatttc agtgtgctgt aatgcatgag gctttgcata atcattatac acagaaatca    660

gtttctaaaa cacaagggaa a                                              681


<210> SEQ ID NO 4
<211> LENGTH: 227
<212> TYPE: PRT
<213> ORGANISM: Artificial Sequence
<220> FEATURE:
<223> OTHER INFORMATION: Amino acid sequence of pFc2

<400> SEQUENCE: 4

Val Gly Arg Pro Cys Pro Ile Cys Pro Ala Cys Glu Gly Pro Gly Pro
1               5                   10                  15

Ser Ala Phe Ile Phe Pro Pro Lys Pro Lys Asp Thr Leu Met Ile Ser
            20                  25                  30

Arg Thr Pro Gln Val Thr Cys Val Val Val Asp Val Ser Gln Glu Asn
        35                  40                  45

Pro Glu Val Gln Phe Ser Trp Tyr Val Asp Gly Val Glu Val His Thr
    50                  55                  60

Ala Gln Thr Arg Pro Lys Glu Ala Gln Phe Asn Ser Thr Tyr Arg Val
65                  70                  75                  80

Val Ser Val Leu Pro Ile Gln His Glu Asp Trp Leu Lys Gly Lys Glu
                85                  90                  95

Phe Glu Cys Lys Val Asn Asn Lys Asp Leu Pro Ala Pro Ile Thr Arg
            100                 105                 110

Ile Ile Ser Lys Ala Lys Gly Pro Ser Arg Glu Pro Gln Val Tyr Thr
        115                 120                 125

Leu Ser Pro Ser Ala Glu Glu Leu Ser Arg Ser Lys Val Ser Ile Thr
    130                 135                 140

Cys Leu Val Thr Gly Phe Tyr Pro Pro Asp Ile Asp Val Glu Trp Lys
145                 150                 155                 160

Ser Asn Gly Gln Pro Glu Pro Glu Gly Asn Tyr Arg Thr Thr Pro Pro
                165                 170                 175

Gln Gln Asp Val Asp Gly Thr Tyr Phe Leu Tyr Ser Lys Leu Ala Val
            180                 185                 190

Asp Lys Ala Ser Trp Gln Arg Gly Asp Pro Phe Gln Cys Ala Val Met
        195                 200                 205

His Glu Ala Leu His Asn His Tyr Thr Gln Lys Ser Val Ser Lys Thr
    210                 215                 220

Gln Gly Lys
225


<210> SEQ ID NO 5
<211> LENGTH: 702
<212> TYPE: DNA
<213> ORGANISM: Artificial Sequence
<220> FEATURE:
<223> OTHER INFORMATION: DNA sequence of pFc3

<400> SEQUENCE: 5

attgagccac cgacacctat ttgtcctgaa atatgctctt gccctgcggc cgaagtttta     60

ggagcaccgt cggtctttct gtttccacct aaacctaagg acattttaat gatctctagg    120

acgcccaagg taacttgtgt tgttgttgat gtttctcaag aagaagctga ggttcaattc    180

tcctggtatg tagacggcgt tcaattgtac accgcacaga ctaggcctat ggaagaacag    240
```

-continued

```
tttaactcaa catacagagt agtgtccgtg ttgccgatcc aacatcaaga ttggttgaaa    300

ggtaaagagt ttaagtgtaa agtgaacaat aaggatctcc tttctcctat taccagaact    360

ataagtaaag ctaccggacc atctcgggtt ccacaggtct acactcttcc accagcttgg    420

gaggagctta gcaagtcaaa ggtaagcatc acttgtctcg taacgggatt ctatccacca    480

gatattgatg tggaatggca gagtaatggt caacaggaac ccgagggtaa ttaccgaaca    540

actcctcctc agcaggatgt tgacggtact tattttcttt attcaaagct agctgttgat    600

aaagtgagat ggcaacgtgg cgatttgttc cagtgcgcag tcatgcatga ggctcttcat    660

aatcactata cacaaaaatc aatttctaag acacaaggga ag                       702
```

```
<210> SEQ ID NO 6
<211> LENGTH: 234
<212> TYPE: PRT
<213> ORGANISM: Artificial Sequence
<220> FEATURE:
<223> OTHER INFORMATION: Amino acid sequence of pFc3

<400> SEQUENCE: 6

Ile Glu Pro Pro Thr Pro Ile Cys Pro Glu Ile Cys Ser Cys Pro Ala
1               5                   10                  15

Ala Glu Val Leu Gly Ala Pro Ser Val Phe Leu Phe Pro Pro Lys Pro
            20                  25                  30

Lys Asp Ile Leu Met Ile Ser Arg Thr Pro Lys Val Thr Cys Val Val
        35                  40                  45

Val Asp Val Ser Gln Glu Glu Ala Glu Val Gln Phe Ser Trp Tyr Val
    50                  55                  60

Asp Gly Val Gln Leu Tyr Thr Ala Gln Thr Arg Pro Met Glu Glu Gln
65                  70                  75                  80

Phe Asn Ser Thr Tyr Arg Val Val Ser Val Leu Pro Ile Gln His Gln
                85                  90                  95

Asp Trp Leu Lys Gly Lys Glu Phe Lys Cys Lys Val Asn Asn Lys Asp
            100                 105                 110

Leu Leu Ser Pro Ile Thr Arg Thr Ile Ser Lys Ala Thr Gly Pro Ser
        115                 120                 125

Arg Val Pro Gln Val Tyr Thr Leu Pro Pro Ala Trp Glu Glu Leu Ser
    130                 135                 140

Lys Ser Lys Val Ser Ile Thr Cys Leu Val Thr Gly Phe Tyr Pro Pro
145                 150                 155                 160

Asp Ile Asp Val Glu Trp Gln Ser Asn Gly Gln Gln Glu Pro Glu Gly
                165                 170                 175

Asn Tyr Arg Thr Thr Pro Pro Gln Gln Asp Val Asp Gly Thr Tyr Phe
            180                 185                 190

Leu Tyr Ser Lys Leu Ala Val Asp Lys Val Arg Trp Gln Arg Gly Asp
        195                 200                 205

Leu Phe Gln Cys Ala Val Met His Glu Ala Leu His Asn His Tyr Thr
    210                 215                 220

Gln Lys Ser Ile Ser Lys Thr Gln Gly Lys
225                 230


<210> SEQ ID NO 7
<211> LENGTH: 21
<212> TYPE: DNA
<213> ORGANISM: Artificial Sequence
<220> FEATURE:
<223> OTHER INFORMATION: 5'UTR of M17 gene
```

<400> SEQUENCE: 7
ggcgtgtgtg tgtgttaaag a 21

<210> SEQ ID NO 8
<211> LENGTH: 272
<212> TYPE: DNA
<213> ORGANISM: Artificial Sequence
<220> FEATURE:
<223> OTHER INFORMATION: DNA sequence of chapherone binding protein(BiP)

<400> SEQUENCE: 8
atggctcgct cgtttggagc taacagtacc gttgtgttgg cgatcatctt cttcggtgag 60
tgattttccg atcttcttct ccgatttaga tctcctctac attgttgctt aatctcagaa 120 cctttttttcg ttgttcctgg atctgaatgt gtttgtttgc aatttcacga tcttaaaagg 180
ttagatctcg attggtattg acgattggaa tctttacgat ttcaggatgt ttatttgcgt 240
tgtcctctgc aatagaagag gctacgaagt ta 272

<210> SEQ ID NO 9
<211> LENGTH: 639
<212> TYPE: DNA
<213> ORGANISM: Artificial Sequence
<220> FEATURE:
<223> OTHER INFORMATION: DNA sequence of FMDV-VP1

<400> SEQUENCE: 9
actacaagta ccggcgaatc tgctgatcca gttactgcta cagttgaaaa ttatggtgga 60
gaaacacaag tgcaaagaag acatcataca gatgtttctt ttatcctaga taggtttgtt 120
aaggtcactc ctaaggattc aattaatgtt ttggacctga tgcagactcc cccacataca 180
ttggttggcg ctctacttcg tactgcaact tattatttcg ctgatttaga ggtagccgtt 240
aaacacgaag gtgatttaac atgggttcct aatggagcac ctgaggctgc actcgataat 300
actactaatc caactgctta ccacaaagca ccactcacta gactcgcgct tccttacact 360
gccccgcata gggttcttgc tactgtttat aacgggaact gcaaatacgc aggtggttca 420
ttgcctaatg tacgaggaga tttgcaagta ttggctcaaa aagcagcatg gccattacct 480
acttctttta actatggagc tataaaggct acacgtgtga cggaacttct ttataggatg 540
aagagagctg agacatactg tcctagacca ttactggctg ttcatccatc cgccgcaaga 600
cacaaacaga aaattgtggc tcccgttaag cagagcctt 639

<210> SEQ ID NO 10
<211> LENGTH: 213
<212> TYPE: PRT
<213> ORGANISM: Artificial Sequence
<220> FEATURE:
<223> OTHER INFORMATION: Amino acid sequence of FMDV-VP1

<400> SEQUENCE: 10

Thr Thr Ser Thr Gly Glu Ser Ala Asp Pro Val Thr Ala Thr Val Glu
1 5 10 15

Asn Tyr Gly Gly Glu Thr Gln Val Gln Arg Arg His His Thr Asp Val
20 25 30

Ser Phe Ile Leu Asp Arg Phe Val Lys Val Thr Pro Lys Asp Ser Ile
35 40 45

Asn Val Leu Asp Leu Met Gln Thr Pro Pro His Thr Leu Val Gly Ala
50 55 60

-continued

```
Leu Leu Arg Thr Ala Thr Tyr Tyr Phe Ala Asp Leu Glu Val Ala Val
65                  70                  75                  80

Lys His Glu Gly Asp Leu Thr Trp Val Pro Asn Gly Ala Pro Glu Ala
                85                  90                  95

Ala Leu Asp Asn Thr Thr Asn Pro Thr Ala Tyr His Lys Ala Pro Leu
            100                 105                 110

Thr Arg Leu Ala Leu Pro Tyr Thr Ala Pro His Arg Val Leu Ala Thr
        115                 120                 125

Val Tyr Asn Gly Asn Cys Lys Tyr Ala Gly Gly Ser Leu Pro Asn Val
    130                 135                 140

Arg Gly Asp Leu Gln Val Leu Ala Gln Lys Ala Ala Trp Pro Leu Pro
145                 150                 155                 160

Thr Ser Phe Asn Tyr Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

Ala Val His Pro Ser Ala Ala Arg His Lys Gln Lys Ile Val Ala Pro
        195                 200                 205

Val Lys Gln Ser Leu
    210


<210> SEQ ID NO 11
<211> LENGTH: 330
<212> TYPE: DNA
<213> ORGANISM: Artificial Sequence
<220> FEATURE:
<223> OTHER INFORMATION: DNA sequence for GP5

<400> SEQUENCE: 11

aacggcaaca gctcgacata ccaatacata tataacttga cggtatgcga gctgaatggg      60

accgcctggt tgtctaccca cttttcttgg gcagtcgaga ccggaggcgg gggtagcaaa     120

aattgtatgg cttgccgcta cgcccgcacc cggttcacca acttcattgt agacgaccgg     180

gggaggattc atcggtggaa gtccccggtg gtggtggaga aatttggcaa agccgaaatt     240

ggcggcggtc ttgtcaccat caaacatgtc gtcctcgaag gggttaaagc tcaacccttg     300

acgaggactt cggctgagca atgggaagcc                                      330


<210> SEQ ID NO 12
<211> LENGTH: 110
<212> TYPE: PRT
<213> ORGANISM: Artificial Sequence
<220> FEATURE:
<223> OTHER INFORMATION: Amino acid sequence for GP5

<400> SEQUENCE: 12

Asn Gly Asn Ser Ser Thr Tyr Gln Tyr Ile Tyr Asn Leu Thr Val Cys
1               5                   10                  15

Glu Leu Asn Gly Thr Ala Trp Leu Ser Thr His Phe Ser Trp Ala Val
            20                  25                  30

Glu Thr Gly Gly Gly Gly Ser Lys Asn Cys Met Ala Cys Arg Tyr Ala
        35                  40                  45

Arg Thr Arg Phe Thr Asn Phe Ile Val Asp Asp Arg Gly Arg Ile His
    50                  55                  60

Arg Trp Lys Ser Pro Val Val Val Glu Lys Phe Gly Lys Ala Glu Ile
65                  70                  75                  80

Gly Gly Gly Leu Val Thr Ile Lys His Val Val Leu Glu Gly Val Lys
                85                  90                  95
```

```
Ala Gln Pro Leu Thr Arg Thr Ser Ala Glu Gln Trp Glu Ala
            100                 105                 110


<210> SEQ ID NO 13
<211> LENGTH: 477
<212> TYPE: DNA
<213> ORGANISM: Artificial Sequence
<220> FEATURE:
<223> OTHER INFORMATION: DNA sequence for CBM3

<400> SEQUENCE: 13

gtatcaggta accttaaggt ggagttttac aactcgaacc cttctgatac aactaactca      60

ataaacccac agttcaaagt tacaaacaca ggcagctctg cgatcgattt gtctaaatta     120

accctcagat actattatac ggttgatgga cagaaggacc agactttctg gtgtgatcat     180

gcagctatca ttggttctaa cggtagctac aacggaatta catcaaacgt gaagggcact     240

ttcgttaaga tgtcctctag cactaacaac gcagacacat atttggagat cagttttacg     300

gggggaaccc ttgaaccagg tgctcacgtc cagattcaag gaagattcgc taaaaacgac     360

tggtcgaact atacccaaag taatgattac agttttaaat ccgcctcaca atttgttgag     420

tgggatcagg tcactgctta cctgaacggg gttctagtgt ggggaaagga acctggt        477


<210> SEQ ID NO 14
<211> LENGTH: 159
<212> TYPE: PRT
<213> ORGANISM: Artificial Sequence
<220> FEATURE:
<223> OTHER INFORMATION: Amino acid sequence for CBM3

<400> SEQUENCE: 14

Val Ser Gly Asn Leu Lys Val Glu Phe Tyr Asn Ser Asn Pro Ser Asp
1               5                   10                  15

Thr Thr Asn Ser Ile Asn Pro Gln Phe Lys Val Thr Asn Thr Gly Ser
            20                  25                  30

Ser Ala Ile Asp Leu Ser Lys Leu Thr Leu Arg Tyr Tyr Tyr Thr Val
        35                  40                  45

Asp Gly Gln Lys Asp Gln Thr Phe Trp Cys Asp His Ala Ala Ile Ile
    50                  55                  60

Gly Ser Asn Gly Ser Tyr Asn Gly Ile Thr Ser Asn Val Lys Gly Thr
65                  70                  75                  80

Phe Val Lys Met Ser Ser Ser Thr Asn Asn Ala Asp Thr Tyr Leu Glu
                85                  90                  95

Ile Ser Phe Thr Gly Gly Thr Leu Glu Pro Gly Ala His Val Gln Ile
            100                 105                 110

Gln Gly Arg Phe Ala Lys Asn Asp Trp Ser Asn Tyr Thr Gln Ser Asn
        115                 120                 125

Asp Tyr Ser Phe Lys Ser Ala Ser Gln Phe Val Glu Trp Asp Gln Val
    130                 135                 140

Thr Ala Tyr Leu Asn Gly Val Leu Val Trp Gly Lys Glu Pro Gly
145                 150                 155


<210> SEQ ID NO 15
<211> LENGTH: 579
<212> TYPE: DNA
<213> ORGANISM: Artificial Sequence
<220> FEATURE:
<223> OTHER INFORMATION: DNA sequence for PCV2

<400> SEQUENCE: 15
```

```
aaaaatggca ttttcaatac acgcctcagt cgaacttttg gatatactgt caagcgtact     60

acagtcacca cgccatcttg ggctgtggat atgatgagat ttaagttgga tgactttgtt    120

cctcctggag ggggaaccaa caaaatttct ataccgtttg agtactatag aatcagaaaa    180

gttaaggttg agttctggcc gtgttccccc ataactcagg gtgatagggg tgtgggttca    240

actgctgtta ttctagatga taacttcgta cctaaggcca acgcattgac ttatgacccc    300

tatgtaaact actcatctag acatacaatc ccacaacctt tctcctacca ctcgcgttat    360

tttacaccaa agcctgtttt agattctacc attgattatt tccaaccaaa taacaagagg    420

aatcagcttt ggttgagatt acaaacctca cggaacgtgg atcatgtcgg attgggtact    480

gcatttgaaa atagtaagta tgatcaggac tacaatatcc gtgtgacaat gtacgttcaa    540

tttagggaat ttaatcttaa agacccacca cttaatcca                           579
```

<210> SEQ ID NO 16
<211> LENGTH: 193
<212> TYPE: PRT
<213> ORGANISM: Artificial Sequence
<220> FEATURE:
<223> OTHER INFORMATION: Amino acid sequence for PCV2

<400> SEQUENCE: 16

```
Lys Asn Gly Ile Phe Asn Thr Arg Leu Ser Arg Thr Phe Gly Tyr Thr
1               5                   10                  15

Val Lys Arg Thr Thr Val Thr Thr Pro Ser Trp Ala Val Asp Met Met
            20                  25                  30

Arg Phe Lys Leu Asp Asp Phe Val Pro Pro Gly Gly Gly Thr Asn Lys
        35                  40                  45

Ile Ser Ile Pro Phe Glu Tyr Tyr Arg Ile Arg Lys Val Lys Val Glu
    50                  55                  60

Phe Trp Pro Cys Ser Pro Ile Thr Gln Gly Asp Arg Gly Val Gly Ser
65                  70                  75                  80

Thr Ala Val Ile Leu Asp Asp Asn Phe Val Pro Lys Ala Asn Ala Leu
                85                  90                  95

Thr Tyr Asp Pro Tyr Val Asn Tyr Ser Ser Arg His Thr Ile Pro Gln
            100                 105                 110

Pro Phe Ser Tyr His Ser Arg Tyr Phe Thr Pro Lys Pro Val Leu Asp
        115                 120                 125

Ser Thr Ile Asp Tyr Phe Gln Pro Asn Asn Lys Arg Asn Gln Leu Trp
    130                 135                 140

Leu Arg Leu Gln Thr Ser Arg Asn Val Asp His Val Gly Leu Gly Thr
145                 150                 155                 160

Ala Phe Glu Asn Ser Lys Tyr Asp Gln Asp Tyr Asn Ile Arg Val Thr
                165                 170                 175

Met Tyr Val Gln Phe Arg Glu Phe Asn Leu Lys Asp Pro Pro Leu Asn
            180                 185                 190

Pro
```

<210> SEQ ID NO 17
<211> LENGTH: 1026
<212> TYPE: DNA
<213> ORGANISM: Artificial Sequence
<220> FEATURE:
<223> OTHER INFORMATION: DNA sequence of E2

<400> SEQUENCE: 17

-continued

```
aacggctagc ctgcaaggaa gattacaggt acgcaatatc atcaaccaat gagatagggc     60

tactcggggc cggaggtctc accaccacct ggaaagaata caaccacgat ttgcaactga    120

atgacgggac cgttaaggcc atttgcgtgg caggttcctt taaagtcaca gcacttaatg    180

tggtcagtag gaggtatttg gcatcattgc ataaggaggc tttacccact tccgtgacat    240

tcgagctcct gttcgacggg accaacccat caactgagga aatgggagat gacttcgggt    300

tcgggctgtg cccgtttgat acgagtcctg ttgtcaaagg aaagtacaat acaaccttgt    360

tgaacggtag tgctttctat cttgtctgtc caatagggtg gacgggtgtt atagagtgca    420

cagcagtgag cccaacaact ctgagaacag aagtggtaaa gaccttcagg agggacaagc    480

cctttccgca cagaatggat tgtgtgacca caacagtgga aaatgaagat ttattctact    540

gtaagttggg gggcaactgg acatgtgtga aaggtgaacc agtggtctac acgggggggc    600

tagtaaaaca atgcagatgg tgtggctttg acttcaatga gcctgacgga ctcccacact    660

accccatagg taagtgcatt ttggcaaatg agacaggtta cagaatagtg gattcaacag    720

actgtaacag agatggtgtt gtaatcagca cagaggggag tcatgagtgc ttgatcggta    780

acacgactgt caaggtgcat gcatcagatg aaagactggg ccccatgcca tgcagaccta    840

aagagatcgt ctctagtgca ggacctgtaa ggaaaacttc ctgtacattc aactacgcaa    900

aaactttgaa gaacaagtac tatgagccca gggacagcta cttccagcaa tatatgctta    960

agggcgagta tcagtactgg tttgacctgg acgtgactga ccgccactca gattacttcg   1020

cagaag                                                              1026
```

<210> SEQ ID NO 18
<211> LENGTH: 341
<212> TYPE: PRT
<213> ORGANISM: Artificial Sequence
<220> FEATURE:
<223> OTHER INFORMATION: Amino acid sequence of E2

<400> SEQUENCE: 18

```
Arg Leu Ala Cys Lys Glu Asp Tyr Arg Tyr Ala Ile Ser Ser Thr Asn
1               5                   10                  15

Glu Ile Gly Leu Leu Gly Ala Gly Gly Leu Thr Thr Thr Trp Lys Glu
            20                  25                  30

Tyr Asn His Asp Leu Gln Leu Asn Asp Gly Thr Val Lys Ala Ile Cys
        35                  40                  45

Val Ala Gly Ser Phe Lys Val Thr Ala Leu Asn Val Val Ser Arg Arg
    50                  55                  60

Tyr Leu Ala Ser Leu His Lys Glu Ala Leu Pro Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Gly Phe Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
        115                 120                 125

Cys Pro Ile Gly Trp Thr Gly Val Ile Glu Cys Thr Ala Val Ser Pro
    130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Thr Val Glu Asn Glu Asp
                165                 170                 175
```

-continued

```
Leu Phe Tyr Cys Lys Leu Gly Gly Asn Trp Thr Cys Val Lys Gly Glu
            180                 185                 190

Pro Val Val Tyr Thr Gly Gly Leu Val Lys Gln Cys Arg Trp Cys Gly
        195                 200                 205

Phe Asp Phe Asn Glu Pro Asp Gly Leu Pro His Tyr Pro Ile Gly Lys
    210                 215                 220

Cys Ile Leu Ala Asn Glu Thr Gly Tyr Arg Ile Val Asp Ser Thr Asp
225                 230                 235                 240

Cys Asn Arg Asp Gly Val Val Ile Ser Thr Glu Gly Ser His Glu Cys
                245                 250                 255

Leu Ile Gly Asn Thr Thr Val Lys Val His Ala Ser Asp Glu Arg Leu
            260                 265                 270

Gly Pro Met Pro Cys Arg Pro Lys Glu Ile Val Ser Ser Ala Gly Pro
        275                 280                 285

Val Arg Lys Thr Ser Cys Thr Phe Asn Tyr Ala Lys Thr Leu Lys Asn
    290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp Arg His Ser
                325                 330                 335

Asp Tyr Phe Ala Glu
            340


<210> SEQ ID NO 19
<211> LENGTH: 429
<212> TYPE: DNA
<213> ORGANISM: Artificial Sequence
<220> FEATURE:
<223> OTHER INFORMATION: DNA sequence of cellulose binding domain

<400> SEQUENCE: 19

tttcgaagtt caccagtgcc tgcacctggt gataacacaa gagacgcata ttctatcatt      60

caggccgagg attatgacag cagttatggt cccaaccttc aaatctttag cttaccaggt     120

ggtggcagcg ccattggcta tattgaaaat ggttattcca ctacctataa aaatattgat     180

tttggtgacg gcgcaacgtc cgtaacagca agagtagcta cccagaatgc tactaccatt     240

caggtaagat tgggaagtcc atcgggtaca ttacttggaa caatttacgt ggggtccaca     300

ggaagctttg atacttatag ggatgtatcc gctaccatta gtaatactgc gggtgtaaaa     360

gatattgttc ttgtattctc aggtcctgtt aatgttgact ggtttgtatt ctcaaaatca     420

ggaacttct                                                             429
```

RECOMBINANT VECTOR COMPRISING PORCINE FC FRAGMENT AND PREPARATION METHOD OF RECOMBINANT PROTEIN USING THEREOF

CROSS-REFERENCE TO RELATED APPLICATION

This application is a Continuation of PCT/KR2018/015398, filed Dec. 6, 2018, which claims the benefit of priority from Korean Patent Application No. 10-2018-0112442, filed Sep. 19, 2018, the contents of each of which are incorporated herein by reference in its entirety.

SEQUENCE LISTING

The Sequence Listing submitted in text format (.txt) filed on Apr. 3, 2019, named "SequenceListing.txt", created on Mar. 1, 2019 (23 KB), is incorporated herein by reference.

TECHNICAL FIELD

The present invention relates to a recombinant vector comprising a porcine Fc fragment, a preparation method of a recombinant protein using the vector, and the like.

Biopharmaceuticals are medical drugs produced using substances present in vivo, and in a broader sense, may be defined as medical drugs produced based on bioengineering techniques such as genetic recombination, cell fusion, cell culture, and the like, which are advanced biotechnology. Such biopharmaceuticals are classified into protein drugs, therapeutic antibodies, vaccines, gene therapeutics, cell therapeutics, and the like. Among them, protein drugs, therapeutic antibodies, and the like are generally produced using a host such as yeast, bacteria, animal cells, insect cells, and the like, and the use of these medical drugs has recently been increasing. Therefore, to efficiently produce these biopharmaceuticals, there is a continuing need to develop a method of increasing the productivity of a recombinant protein, facilitating the isolation thereof, and increasing the stability of a recombinant protein.

Meanwhile, the remarkable development of molecular biology and genetic engineering techniques has been applied to the field of plants, and thus efforts have been steadily continuing to produce useful physiologically active substances from plants. Production of useful substances from plants may significantly reduce production costs, fundamentally exclude various contaminants (viruses, oncogenes, enterotoxins, and the like) that may be generated using general methods (methods of synthesizing proteins from animal cells or microorganisms, and isolating and purifying them), and enables the management of seed stock using seeds even in a commercialization process unlike animal cells or microorganisms (Korean Patent Registration No. 10-1732624).

Therefore, if there is a recombinant protein production system that can be used even in plants and significantly increase the productivity of recombinant proteins, and facilitates the separation and storage of recombinant proteins by increasing solubility and stability thereof, it is anticipated to enable highly efficient production of recombinant proteins needed in various fields.

DISCLOSURE

Technical Problem

The present invention has been made to address the above-described problems, and it is an object of the present invention is to provide a recombinant vector comprising a porcine Fc fragment, a preparation method a recombinant protein using the vector, and the like.

However, technical problems to be solved by the present invention are not limited to the above-described technical problems, and other unmentioned technical problems will become apparent from the following description to those of ordinary skill in the art.

Technical Solution

The present invention provides a recombinant vector comprising a polynucleotide encoding a porcine Fc fragment represented by SEQ ID NO: 4 and a polynucleotide encoding a target protein.

In one embodiment of the present invention, in the recombinant vector, a promoter gene, the polynucleotide encoding an Fc fragment, and the polynucleotide encoding a target protein; or a promoter gene, the polynucleotide encoding a target protein, and the polynucleotide encoding an Fc fragment may be sequentially linked in this order.

In another embodiment of the present invention, a promoter may be a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, a pEMU promoter, an MAS promoter, a histone promoter, a Clp promoter, or the like, but is not particularly limited as long as the promoter is a known promoter.

In another embodiment of the present invention, the target protein may be an antigen, an antibody, an antibody fragment, a structural protein, a regulatory protein, a transcription factor, a toxin protein, a hormone, a hormone analogue, a cytokine, an enzyme, an enzyme fragment, an enzyme inhibitor, a transport protein, a receptor, a fragment of a receptor, a bio-defense inducer, a storage protein, a movement protein, an exploitive protein, or a reporter protein, but target protein is not particularly limited as long as it is a protein that can be produced by the recombinant vector.

In another embodiment of the present invention, the recombinant vector may further include a polynucleotide encoding a chaperone binding protein (BiP), a gene encoding a His-Asp-Glu-Leu (HDEL) peptide, a 5' untranslated region (UTR) site gene of M17, or the like.

In another embodiment of the present invention, the recombinant vector increases an expression amount of a target protein to which an Fc fragment as a tag is fused and increases the solubility of the target protein. The fusion may be a form in which the target protein is linked to the N-terminus and/or the C-terminus of the Fc fragment via a peptide bond, but the present invention is not limited thereto, and any form in which the Fc fragment is bound to the target protein is possible.

The present invention also provides a transgenic organism transformed with the recombinant vector.

In one embodiment of the present invention, the transgenic organism may be a microorganism such as *Escherichia coli, Bacillus, Salmonella*, yeast, or the like, insect cells, animal cells including human cells, an animal such as a mouse, a rat, a dog, a monkey, a pig, a horse, a cow, or the like, *Agrobacterium tumefaciens*, a plant, or the like, and examples of the plant include food crops including rice, wheat, barley, corn, beans, potatoes, red beans, oats, and sorghum; vegetable crops including *Arabidopsis thaliana*, Chinese cabbage, white radish, peppers, strawberries, tomatoes, water melons, cucumbers, cabbage, oriental melons, pumpkins, spring onions, onions, and carrots; special purpose crops including ginseng, tobacco, cotton, sesame, sugarcane, sugar beets, perilla, peanuts, and rape; fruit crops including apple trees, pear trees, jujube trees, peaches, grapes, tangerines, persimmons, plums, apricots, and bananas; and flowers including roses, carnations, chrysanthemums, lilies, and tulips, but the present invention is not limited thereto, and any living body capable of being transformed with the recombinant vector of the present invention may be used.

The present invention also provides a preparation method of a recombinant protein, which includes (a) culturing the transgenic organism; and (b) isolating an Fc fragment-fused target protein from the transgenic organism or the culture broth and purifying the target protein. The transgenic organism may be preferably a cell itself or a cell-containing culture, and the culture broth may be preferably a culture broth obtained by culturing cells and removing the cells, but the present invention is not limited thereto, and any culture broth including the recombinant protein of the present invention is possible.

The present invention also provides a composition for tagging a target protein, which includes a porcine Fc fragment represented by SEQ ID NO: 4 as an active ingredient.

The present invention also provides a use of a porcine Fc fragment represented by SEQ ID NO: 4 for tagging a recombinant protein.

The present invention also provides a method of binding a porcine Fc fragment to a recombinant protein, which includes binding a porcine Fc fragment represented by SEQ ID NO: 4 to a recombinant protein.

In one embodiment of the present invention, the method increases stability of the recombinant protein.

Advantageous Effects

A recombinant vector comprising a porcine Fc fragment according to the present invention not only increases the productivity of a target protein but also increases solubility and stability thereof by fusing a pFc fragment with various target proteins, facilitating isolation and storage of a recombinant protein, and thus can be widely applied to target proteins having various activities and therefore is expected to enable highly efficient production of recombinant proteins in various fields.

BEST MODE

Figure 1:
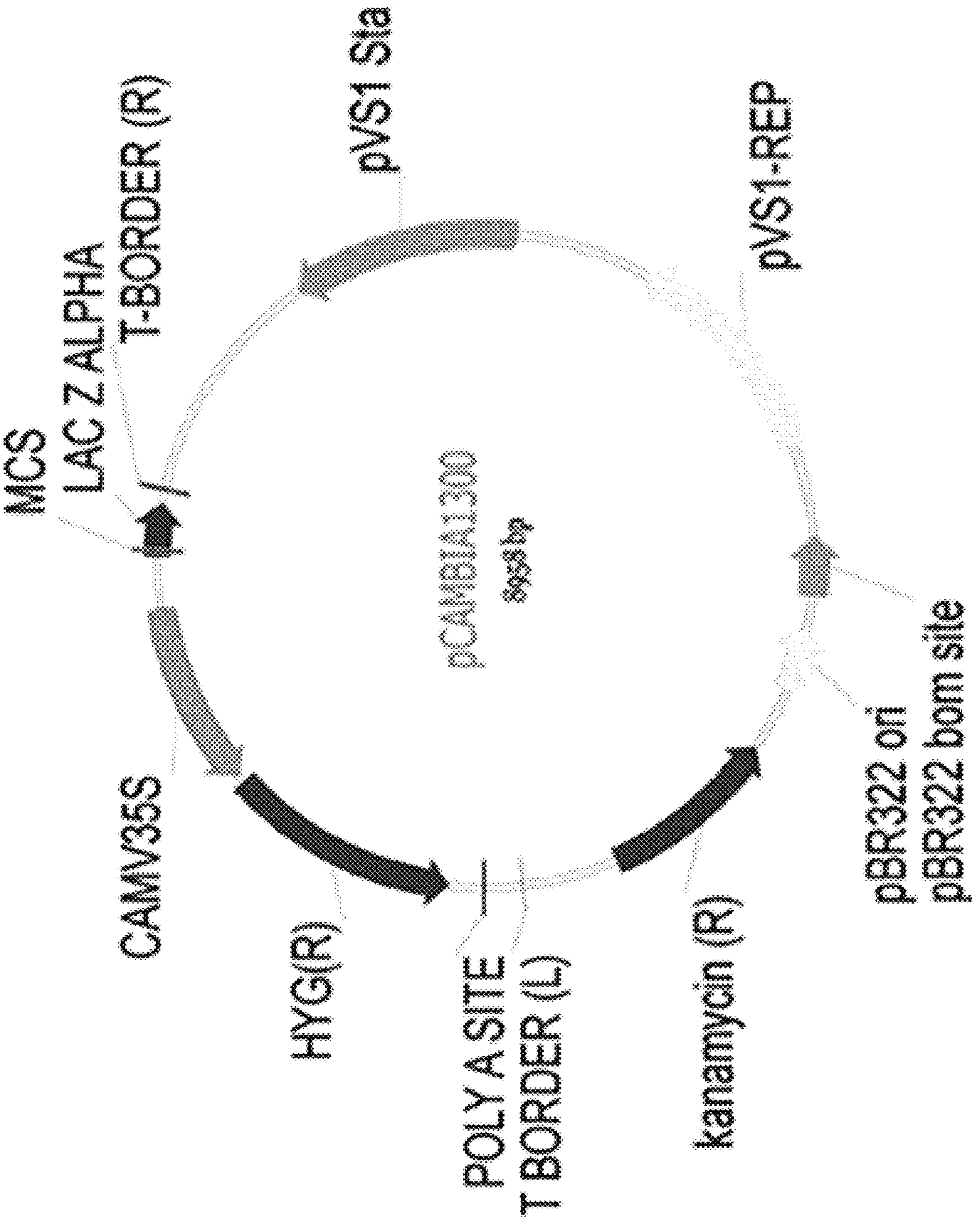
FIG. 1 is a view illustrating a pCAMBIA1300 vector map according to an embodiment of the present invention.

In the present invention, it has been confirmed that when a porcine immunoglobulin Fc fragment is bound to various physiologically active proteins, antigens, peptides, and the like, not only an expression amount and productivity of proteins but also the solubility and stability of proteins can be increased by the fragment, and it is an object of the present invention is to provide a recombinant vector comprising a polynucleotide encoding the porcine Fc fragment and a preparation method of a recombinant protein using the recombinant vector.

As used herein, the term "Fc fragment" refers to a Fc fragment not having an antigen binding site, in which only a heavy chain (H chain) portion is linked by a S—S bond, when an immunoglobulin is digested with papain, and the Fc fragment of the present invention is preferably a porcine Fc fragment, more preferably a porcine Fc fragment represented by SEQ ID NO: 4, but the present invention is not limited thereto, and any Fc fragment that increases the expression amount and solubility of a target protein when fused with the target protein may be used. In addition, a variant of the Fc fragment of SEQ ID NO: 4 of the present invention is within the scope of the present invention. Specifically, the gene may include a base sequence having 90% or more, preferably 95% or more, and more preferably 98% or more sequence homology to the base sequence of SEQ ID NO: 3. The "% sequence homology" with respect to a polynucleotide is determined by comparing optimally-arranged sequences with a comparative region, and a part of the polynucleotide sequence in the comparative region may include an addition or deletion (i.e., a gap) compared to a reference sequence (without an addition or deletion) with respect to the optimal arrangement of the sequences.

As used herein, the term "target protein" refers to a protein to be produced using a genetic engineering method, and the target protein may be preferably commercially available proteins in need of mass production and more preferably, an antigen, an antibody, an antibody fragment, a structural protein, a regulatory protein, a transcription factor, a toxin protein, a hormone, a hormone analogue, a cytokine, an enzyme, an enzyme fragment, an enzyme inhibitor, a transport protein, a receptor, a receptor fragment, a biodefense inducer, a storage protein, a movement protein, an exploitive protein, or a reporter protein, but the present invention is limited thereto, and any protein capable of being produced with the recombinant vector of the present invention may be used.

As used herein, the term "recombinant vector" refers to a vector capable of expressing a peptide or protein encoded by a heterologous nucleic acid inserted into the vector, and preferably means a vector constructed so as to express a porcine Fc fragment-fused target protein. The term "vector" as used herein refers to any vehicle for the introduction and/or transfer of a base into a host cell in vitro, ex vivo, or in vivo, and may mean a replicon to which another DNA fragment may be attached so as to bring about the replication of the attached fragment. The term "replicon" refers to any genetic unit (e.g., a plasmid, a phage, a cosmid, a chromosome, a virus, and the like) that functions as an autonomous unit of DNA replication in vivo, i.e., is capable of replicating by self-regulation. The recombinant vector of the present invention may preferably include a promoter which is a transcription initiation factor to which an RNA polymerase binds, an arbitrary operator sequence for regulating transcription, a sequence encoding a suitable mRNA ribosome binding site, a sequence regulating the termination of transcription and translation, a terminator, or the like. More preferably, the recombinant vector may further include a 5' UTR site gene of M17, a BiP gene for transporting a target protein to a vesicle, a HDEL gene for minimizing the degradation of a protein so that the protein can be stably maintained in a vesicle, or the like. More preferably, the recombinant vector may further include a gene for an additional tag for easily isolating a recombinant protein other than an Fc fragment, which is a tag, a marker gene for selecting an antibiotic-resistant gene or the like to select a transgenic organism, or the like.

The gene for a tag may be additionally included for easy separation, other than the Fc fragment of the present invention, which is a tag protein, and examples thereof may include an Avi tag, a Calmodulin tag, a polyglutamate tag, an E tag, a FLAG tag, a HA tag, a His tag, a Myc tag, an S tag, an SBP tag, an IgG-Fc tag, a CTB tag, a Softag 1 tag, a Softag 3 tag, a Strep tag, a TC tag, a V5 tag, a VSV tag, an Xpress tag, and the like. Examples of the marker gene for selection may include genes resistant to herbicide such as glyphosate and phosphinothricin, genes resistant to antibiotics such as kanamycin, G418, bleomycin, hygromycin, and chloramphenicol, the aadA gene, and the like, examples of the promoter may include a pEMU promoter, an MAS promoter, a histone promoter, a Clp promoter, a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, an elongation factor-1 alpha (EF-1$\alpha$) promoter, and the like, and examples of the terminator may include nopaline synthase (NOS), a rice amylase RAmyl A terminator, a phaseolin terminator, an Octopine gene terminator of *Agrobacterium tumefaciens*, and an *E. coli* rrnB1/B2 terminator, but the present invention is not limited thereto, and any gene used in known recombinant vectors may be used.

As used herein, the term "fusion protein" refers to a recombinant protein produced by fusion of a porcine Fc fragment and a target protein, and preferably means a recombinant protein with enhanced solubility through fusion with the Fc fragment, but the present invention is not limited thereto, and any recombinant protein produced through binding with a porcine Fc fragment may be used.

As used herein, the term "transformation" collectively refers to changes in the genetic properties of an organism by injected DNA, and the term "transgenic organism" refers to a living organism produced by injecting an external gene using a molecular genetic method, and preferably means a living organism transformed by the recombinant vector of the present invention. The living organism is not particularly limited as long as it is a living organism such as microorganisms, eukaryotic cells, insects, animals, plants, and the like, and examples thereof include, but are not limited to, *E. coli, Salmonella, Bacillus*, yeast, animal cells, mice, rats, dogs, monkeys, pigs, horses, cows, *Agrobacterium tumefaciens*, and plants. The transgenic organism may be produced using a method such as transformation, transfection, an *Agrobacterium*-mediated transformation method, particle gun bombardment, sonication, electroporation, and a polyethylene glycol (PEG)-mediated transformation method, but the present invention is not limited thereto, and any method capable of injecting the vector of the present invention may be used.

As used herein, the term "solubility" refers to a degree to which a target protein or a peptide can be dissolved in a solvent suitable for administration to the human body. Specifically, the solubility may indicate a degree to which a solute is saturated with respect to a given solvent at a particular temperature. The solubility may be measured by determining the saturation concentration of a solute, for example, by adding an excess amount of a solute to a solvent and stirring and filtering the solution, and then measuring the concentration thereof using a UV spectrometer, HPLC, or the like, but the present invention is not limited thereto. High solubility is more suitable for the isolation and purification of recombinant proteins, and inhibits the agglomeration of recombinant proteins, and thus it is effective in maintaining the physiological activity or pharmacological activity of recombinant proteins.

Hereinafter, exemplary embodiments will be described to aid in understanding the present invention. However, the following examples are provided only to facilitate the understanding of the present invention and are not intended to limit the scope of the present invention.

EXAMPLES

Figure 2:
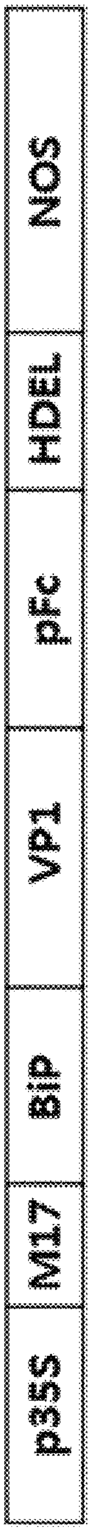
FIG. 2 is a view illustrating arrangement of genes for expressing a pFc-fused VP1 recombinant protein according to an embodiment of the present invention.

Example 1: Preparation of pFc-Fused VP1 Recombinant Protein Expression Vector To prepare a recombinant vector for producing a recombinant protein with increased separation and purification efficiency through an increase in expression amount of a target protein and enhancement of the solubility thereof, pFc1 (SEQ ID NO: 1), pFc2 (SEQ ID NO: 3), or pFc3 (SEQ ID NO: 5) of a porcine Fc fragment (pFc) was used to construct a recombinant vector. More specifically, as illustrated in FIGS. 1 and 2, a 5' untranslated region (UTR) site gene (SEQ ID NO: 7) of M17, a polynucleotide (SEQ ID NO: 8) encoding a chaperone binding protein (BiP), a VP1 gene (SEQ ID NO: 9) of the foot-and-mouth disease virus (FMDV), a polynucleotide encoding a pFc, and a polynucleotide encoding a His-Asp-Glu-Leu (HDEL) protein were sequentially cloned into between a CaMV 35S promoter gene and an NOS terminator of a pCAMBIA1300 vector, thereby completing the preparation of a recombinant vector. For the pFc fragment, different recombinant vectors were prepared by inserting pFc1, pFc2, or pFc3.

Example 2: Experiment for pFc-Fused VP1 Recombinant Protein Expression 2.1. Experiment for Confirming Expression Amount of pFc-Fused VP1 Recombinant Protein To identify protein expression amounts of a pFc-fused VP1 recombinant protein expression vector prepared in the same manner as in Example 1, the vector was introduced into a protoplast isolated from *Arabidopsis* leaves by PEG-mediated transformation to prepare a transgenic organism, and then the cultured protoplast was collected and lysed, and an expression pattern of BiP:FMDV-VP1:pFc, which is a recombinant protein expressed therefrom, was confirmed by western blotting using a pFc-recognizing anti-pig secondary antibody (1:5,000, Abcam). More specifically, 30 μL of a cell lysate was mixed with an SDS sample buffer and then heated. Then, proteins were separated on a 10% SDS-PAGE gel according to size by electrophoresis, the separated proteins were transferred to a PVDF membrane, followed by blocking using 5% skim milk, and then the proteins were subjected to binding to antibodies and treated with an ECL solution using a method provided by a manufacturer to identify pFc-fused recombinant proteins. The results thereof are illustrated in FIG. 3.

Figure 3:
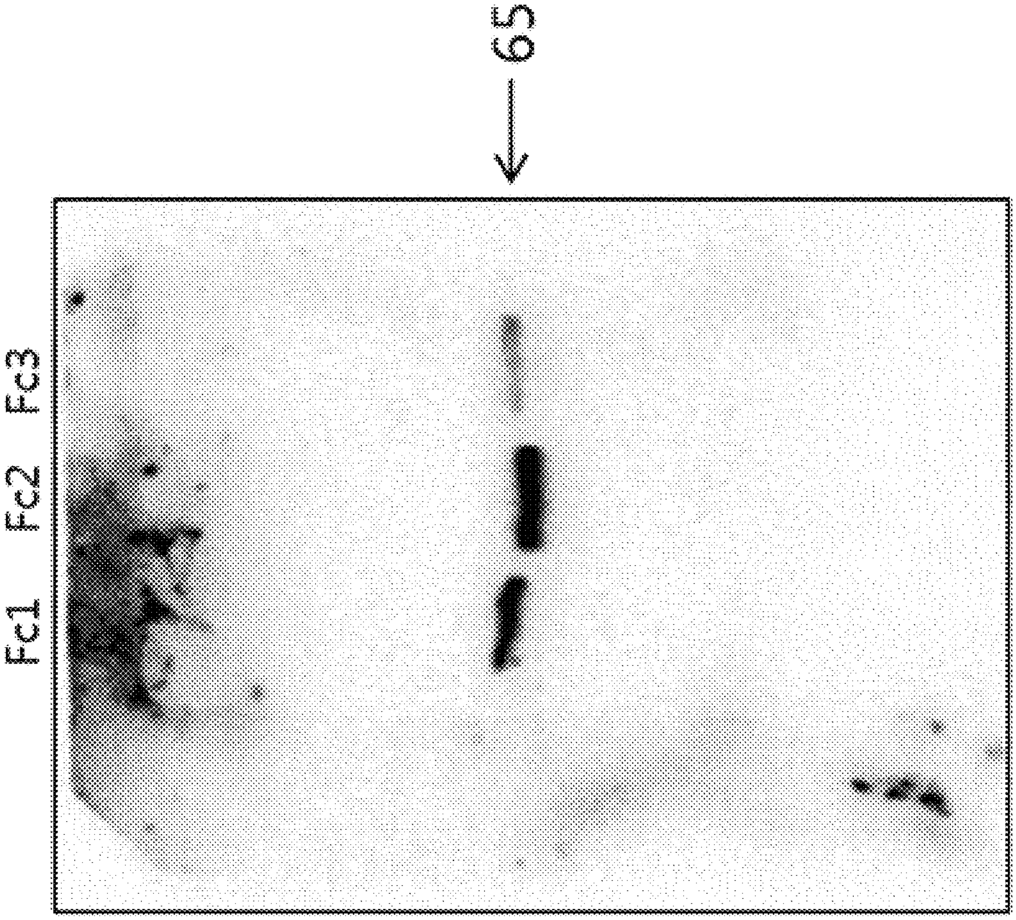
FIG. 3 illustrates western blotting results of confirming an expression amount of a pFc-fused VP1 recombinant protein according to an embodiment of the present invention.

As illustrated in FIG. 3, it was confirmed that the expression amount of the pFc2-fused recombinant protein was highest among the recombinant proteins fused with various pFc fragments. From the above results, it was confirmed that the same immunoglobulin fragments did not exhibit the same effect.

2.2. Stability Confirmation Experiment for pFc-Fused VP1 Recombinant Protein

To confirm the stability of proteins of a pFc-fused recombinant protein expression vector prepared in the same manner as in Example 1, a sample (0) at the time of extracting the recombinant proteins and a sample (1) obtained after storage at 4° C. for 1 hour were examined by western blotting using the same method as that used in Example 2.1. The results thereof are illustrated in FIG. 4.

Figure 4:
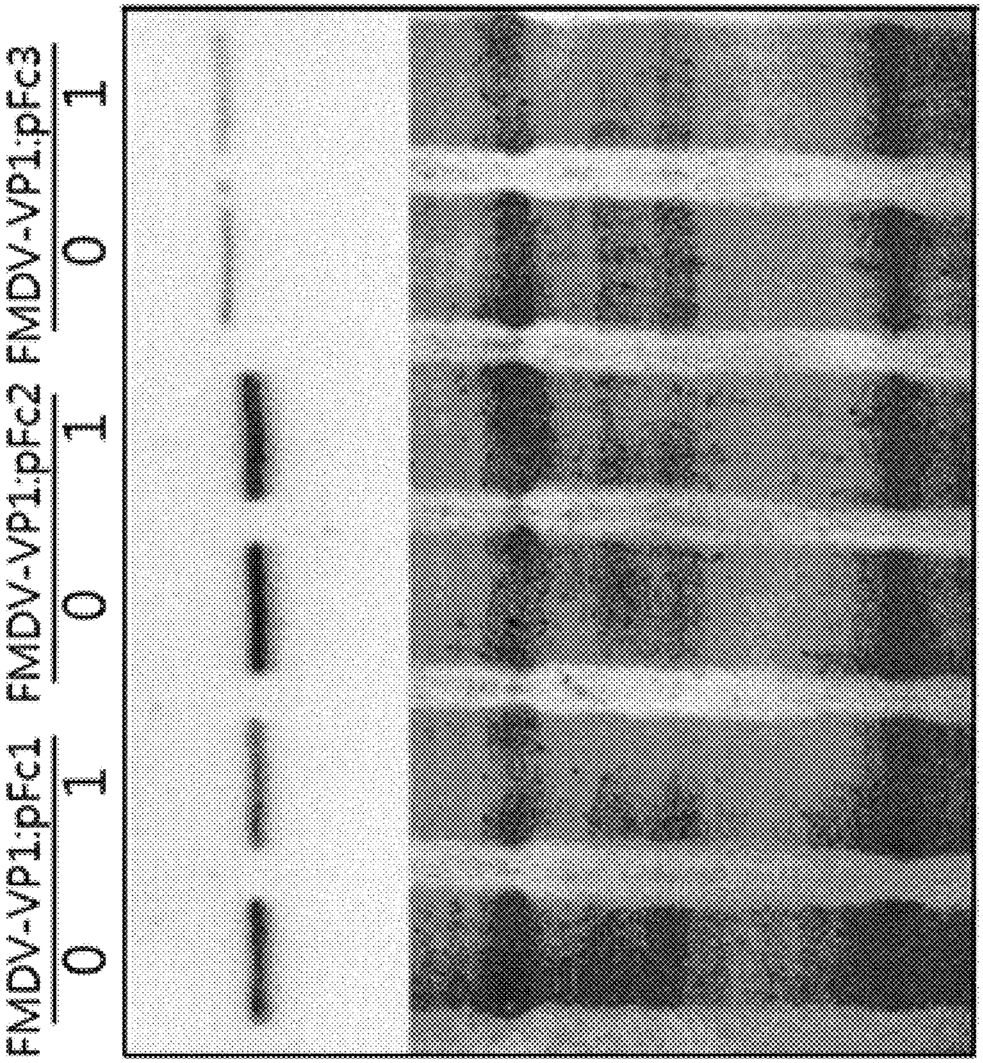
FIG. 4 illustrates western blotting results of confirming the stability of a pFc-fused VP1 recombinant protein according to an embodiment of the present invention.

As illustrated in FIG. 4, it was confirmed that the pFc2-fused recombinant protein exhibited the greatest expression amount and high stability.

2.3. Solubility Confirmation Experiment for pFc2-Fused VP1 Recombinant Protein

To confirm the solubility of proteins of a pFc2-fused recombinant protein expression vector prepared in the same manner as in Example 1, leaves of *Nicotiana benthamiana* were inoculated with *Agrobacterium tumefaciens* transformed with the vector to express the pFc2-fused recombinant protein (BiP:FMDV-VP1:pFc2) using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, recombinant proteins produced through fusion of a polynucleotide (SEQ ID NO: 13) encoding a known cellulose binding module (CBM3) instead of the pFc fragment was used. The results thereof are illustrated in FIG. 5.

Figure 5:
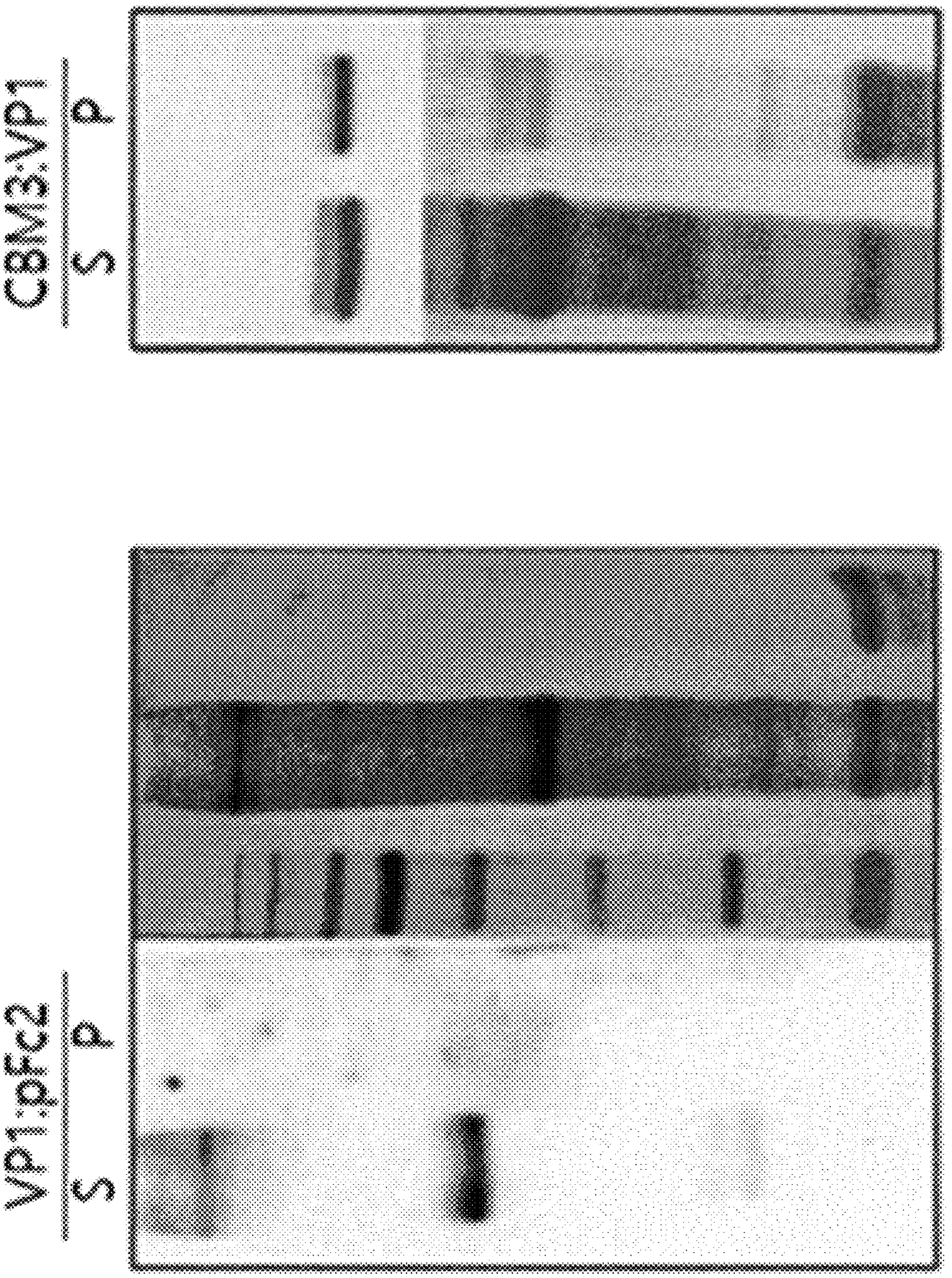
FIG. 5 illustrates western blotting results of confirming the solubility of a pFc-fused VP1 recombinant protein according to an embodiment of the present invention.

As illustrated in FIG. 5, it was confirmed that the pFc2-fused recombinant protein was not observed in the pellet portion, while being included in the solution. However, in the case of the CBM3-fused recombinant proteins, a considerable number of recombinant proteins were observed in the pellet portion. From the above results, it was confirmed that the pFc2-fused recombinant protein exhibited increased solubility through structural modification due to binding between a target protein and a pFc2 fragment, from which it was confirmed that the pFc2-fused recombinant protein was more effective in isolation and purification, and was effective in maintaining physiological activity or pharmacological activity due to inhibition of the agglomeration of the recombinant protein.

Example 3: Solubility Confirmation Experiment for pFc2-Fused GP5 Recombinant Antigen To fuse the pFc2 fragment with a GP5 antigen protein of porcine reproductive and respiratory syndrome (PRRS), a polynucleotide (SEQ ID NO: 11) encoding the porcine GP5 antigen protein was inserted instead of the VP1 gene of FMDV included in the recombinant vector of Example 1 to prepare a recombinant vector expressing a GP5:pFc2 recombinant antigen. Then, leaves of *Nicotiana benthamiana* were inoculated with *Agrobacterium tumefaciens* transformed with the vector to express the pFc2-fused GP5 recombinant antigen (GP5:pFc2) using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, a GP5 recombinant antigen fused with CBM3 (SEQ ID NO: 14) instead of the pFc fragment was used, and in the case of the CBM3-fused GP5 recombinant antigen, an experiment was carried out using an HA antibody for western blotting. The results thereof are illustrated in FIG. 6.

Figure 6:
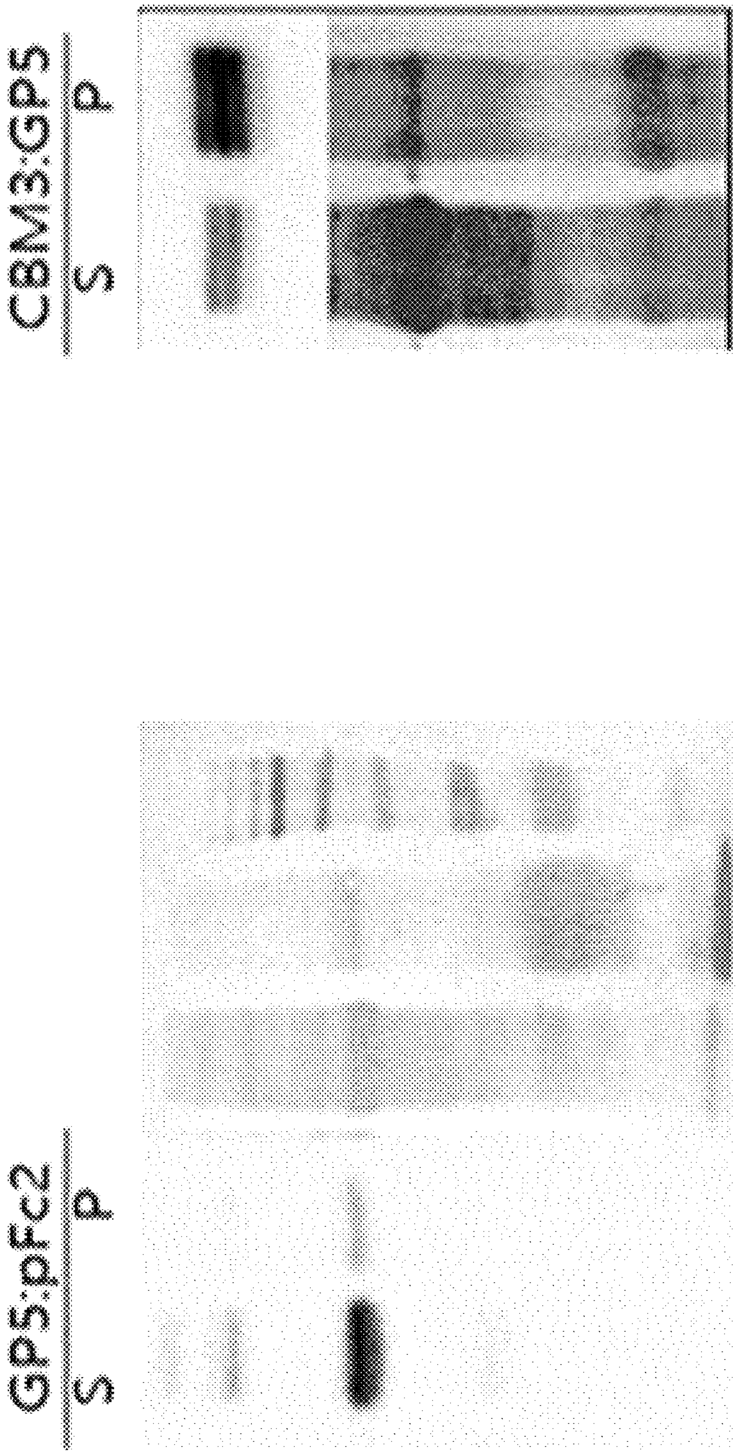
FIG. 6 illustrates western blotting results of confirming the solubility of pFc-fused GP5 recombinant antigen according to an embodiment of the present invention.

As illustrated in FIG. 6, it was confirmed that in the case of the pFc2-fused GP5 recombinant antigen, while some proteins were observed in the pellet portion, most proteins were included in the solution. In contrast, in the case of the CBM3-fused GP5 recombinant antigen, a considerable number of recombinant proteins were observed in the pellet portion. From the above results, it was confirmed that the pFc2-fused recombinant protein exhibited increased solubility regardless of the type of protein.

From these results, it was confirmed that by fusing a porcine Fc fragment, especially a pFc2 fragment including an amino acid sequence represented by SEQ ID NO: 4 with a target protein, the expression amount and solubility of the target protein were increased, and thus the target protein could be stably and easily separated and stored.

Example 4: Productivity and Solubility Confirmation Experiment for pFc2-Fused PCV2 Recombinant Protein To fuse the pFc2 fragment with a porcine circovirus type 2 (PCV2) protein, a polynucleotide (SEQ ID NO: 15) encoding the PCV2 protein was inserted instead of the VP1 gene of FMDV included in the recombinant vector of Example 1 to prepare a recombinant vector expressing a PCV2:pFc2 recombinant protein. Then, leaves of *Nicotiana benthamiana* were inoculated with *Agrobacterium tumefaciens* transformed with the vector to express the pFc2-fused PCV2 recombinant protein using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, a PCV2 recombinant protein fused with His-tag instead of the pFc fragment was used, and in the case of the His-tag-fused PCV2 recombinant protein, an experiment was carried out using an anti-His antibody for western blotting. The results thereof are illustrated in FIG. 7.

Figure 7:
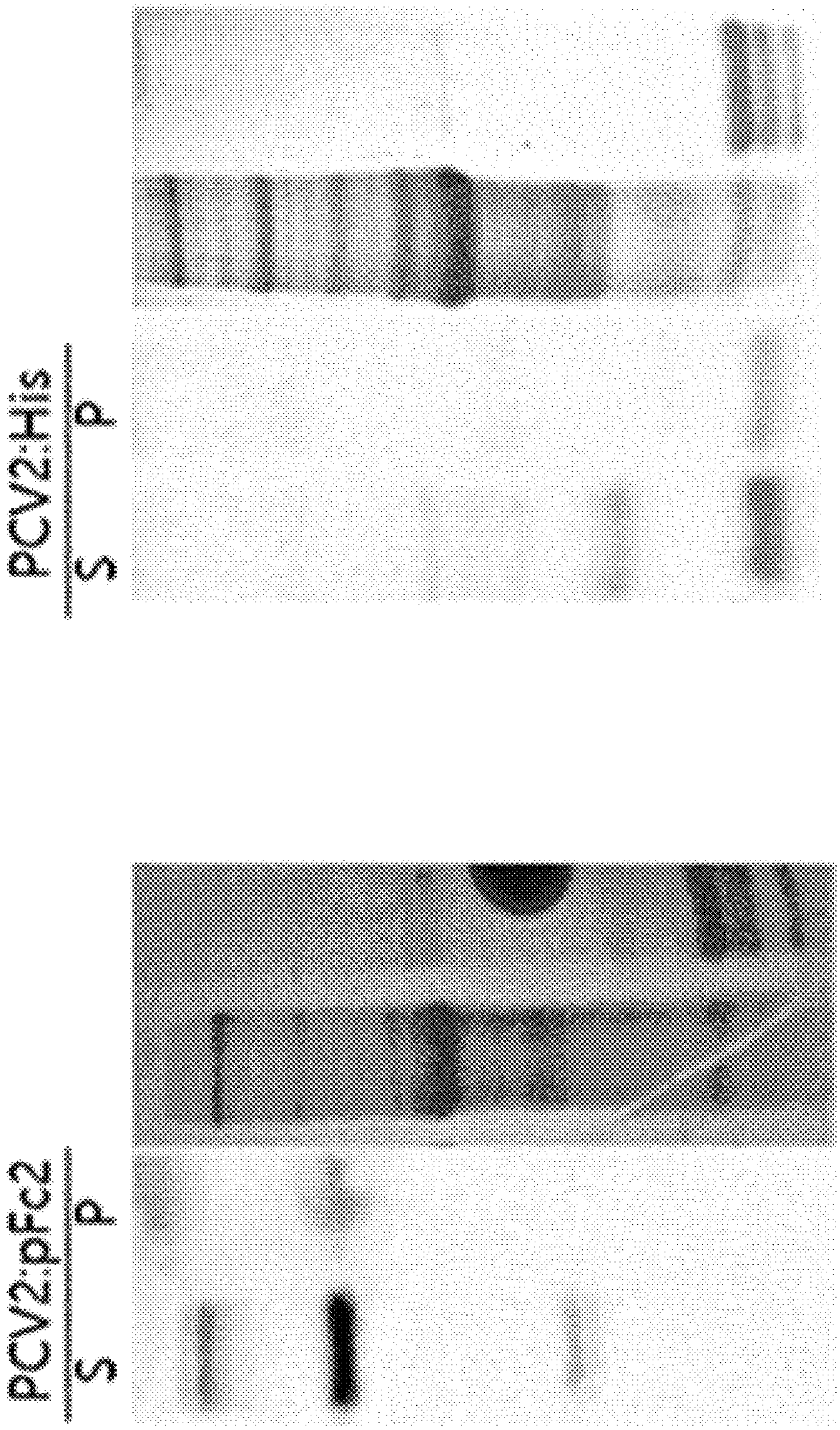
FIG. 7 illustrates western blotting results of confirming the solubility and productivity of a pFc-fused PCV2 recombinant protein according to an embodiment of the present invention.

As illustrated in FIG. 7, it was confirmed that the pFc2-fused PCV2 recombinant protein was mostly included in the solution and exhibited significantly increased productivity as compared to that of the His-tag-fused PCV2 recombinant protein.

Example 5: Experiment for pFc2-Fused E2 Recombinant Protein Expression

To confirm whether the pFc2 fragment is fused to an antigen protein and usable, a polynucleotide (SEQ ID NO: 17) encoding an E2 protein, which is a swine fever antigen, was inserted instead of the VP1 gene of FMDV included in the recombinant vector of Example 1 to prepare a recombinant vector expressing a BiP:E2:pFc2 recombinant protein. Then, *Arabidopsis thaliana* was transformed with the prepared recombinant vector by an *Agrobacterium*-mediated transformation method, *Arabidopsis thaliana* with resistance to kanamycin was selected, and homo-seeds in which the pFc2-fused E2 recombinant protein was stably expressed through generation advancement were finally obtained, thereby completing the preparation of a transformed plant. Then, proteins were isolated from 8 g of the finally obtained transformed plant by using a protein extraction buffer commonly used in protein extraction, and the pFc-fused E2 recombinant protein was isolated using AKTA prime (GE Healthcare) equipped with a Protein A-Sepharose column. Then, as a control, a BiP:E2:CBD recombinant protein produced by fusion of a CBD (SEQ ID NO: 19) instead of the pFc fragment was used. The CBD-fused E2 recombinant protein was isolated from 5 g of the transformed plant using amorphous cellulose (AMC). Thereafter, the isolated recombinant protein was dialyzed with phosphate buffered saline (PBS), and then concentrated using a centrifugal filter tube. To measure the amount of the isolated recombinant protein, the protein was subjected to SDS-PAGE and then Coomassie Blue staining. At this time, the recombinant protein was quantified using a standard curve using bovine serum albumin (BSA). The results thereof are illustrated in FIG. 8.

Figure 8:
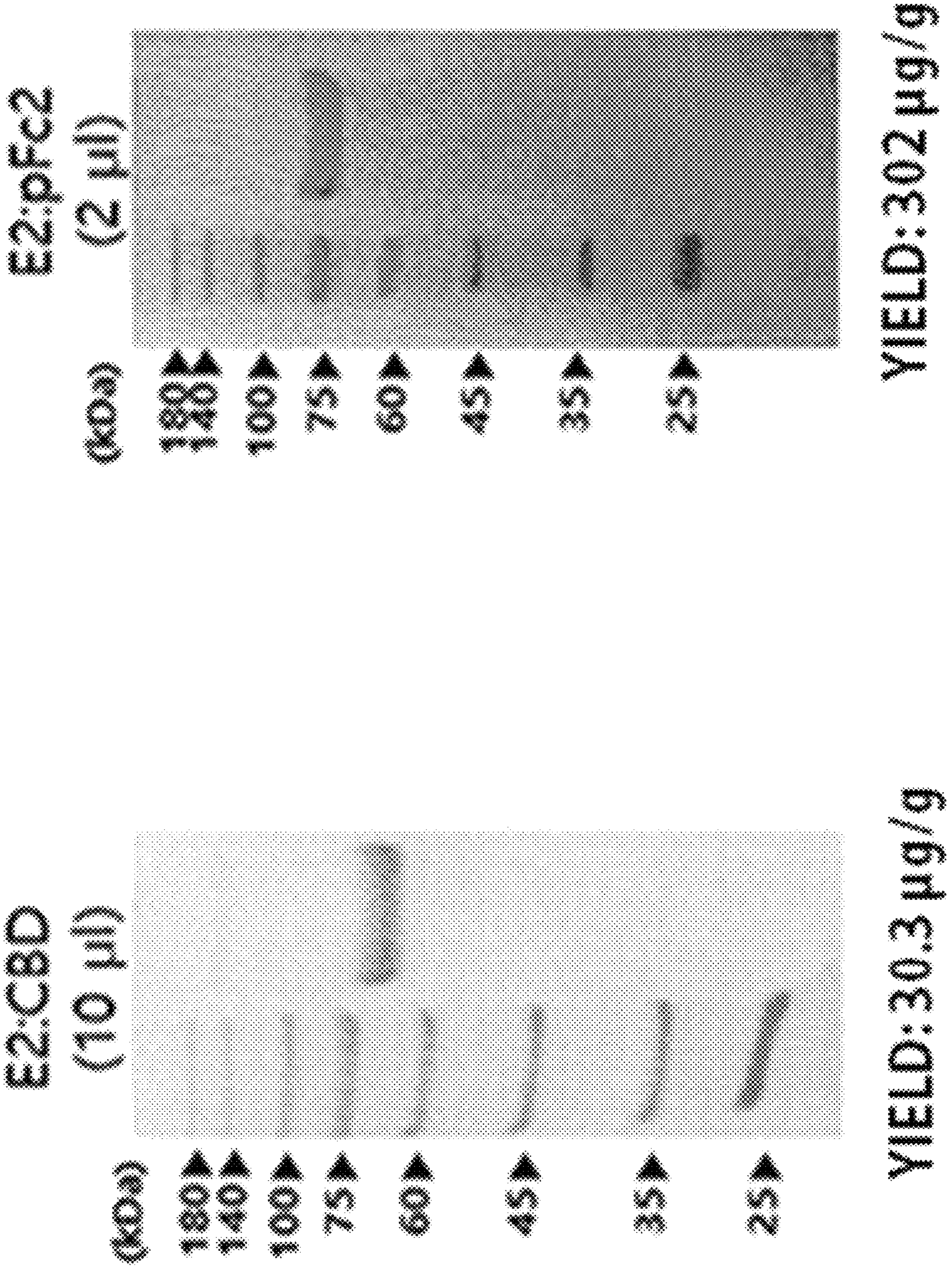
FIG. 8 illustrates results of confirming the productivity of a pFc-fused E2 recombinant antigen according to an embodiment of the present invention.

As illustrated in FIG. 8, it was confirmed that while the CBD-fused E2 recombinant antigen was produced in an amount of about 30 μg per 1 g of the plant, the pFc2-fused E2 recombinant antigen was produced in an amount of 302 μg per 1 g of the plant. From the above results, it was confirmed that an expression amount of a target antigen could be increased 10-fold or more using the pFc2 fragment.

From the above results, it was confirmed that by fusing the pFc2 fragment, which is a tag, of the present invention with various target proteins, not only the productivity of a target protein may be significantly increased, but also the solubility and stability thereof may be increased, inhibiting agglomeration of the target protein, and thus pFc2-fused target proteins are significantly effective in efficient production of recombinant proteins.

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

The present invention relates to a recombinant vector comprising a porcine Fc fragment, and by fusing the porcine Fc fragment with various target proteins by using the recombinant vector of the present invention, various protein may be expressed using various hosts including plants, and the productivity and stability of a target protein may be significantly increased by binding of the Fc fragment of the present invention as a tag, and thus it is anticipated that the recombinant vector may be widely used in the preparation of various commercialized target proteins.

The invention claimed is:

1. A method of tagging a target protein with a porcine Fc fragment, the method comprising culturing a transgenic host cell transformed with a recombinant expression vector comprising a DNA sequence encoding the porcine Fc fragment consisting of the sequence set forth in SEQ ID NO:4 operably linked to a DNA sequence encoding the target protein, in a suitable condition to express a porcine Fc fragment-fused target protein.

2. The method of claim 1, wherein the recombinant expression vector further comprises a promoter, and the promoter, the DNA sequence encoding the porcine Fc fragment, and the DNA sequence encoding the target protein are sequentially linked in order.

3. The method of claim 2, wherein the promoter comprises one or more selected from the group consisting of a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, a pEMU promoter, an MAS promoter, a histone promoter, a Clp promoter, and an elongation factor-1 alpha (EF-1$\alpha$) promoter.

4. The method of claim 1, wherein the recombinant expression vector further comprises a DNA sequence encoding a chaperone binding protein.

5. The method of claim 1, wherein the recombinant expression vector further comprises a gene encoding a His-Asp-Glu-Leu (HDEL) (SEQ ID NO:20) peptide.

6. The method of claim 1, wherein the recombinant expression vector increases an expression amount and solubility of the Fc fragment-fused target protein, compared to a His-tag-fused target protein as a control.

7. The method of claim 1, wherein the recombinant expression vector further comprises a 5' untranslated region (UTR) sequence of an M17 gene.

* * * * *